(12) United States Patent
Klews et al.

(10) Patent No.: US 9,914,226 B2
(45) Date of Patent: Mar. 13, 2018

(54) BIDIRECTIONAL PIVOTING JOINT, AND A HOLDING AND POSITIONING DEVICE WHICH COMPRISES A PLURALITY OF SAID PIVOTING JOINTS

(75) Inventors: Peter-Michael Klews, Barum (DE); Kerstin Ahrens, Marschacht (DE); Marko Behr, Tespe (DE)

(73) Assignee: Peter-Michael Klews, Barum (DE)

( * ) Notice: Subject to any disclaimer, the term of this patent is extended or adjusted under 35 U.S.C. 154(b) by 580 days.

(21) Appl. No.: 14/402,052

(22) PCT Filed: Jun. 15, 2012

(86) PCT No.: PCT/EP2012/002590
§ 371 (c)(1),
(2), (4) Date: Nov. 18, 2014

(87) PCT Pub. No.: WO2013/185791
PCT Pub. Date: Dec. 19, 2013

(65) Prior Publication Data
US 2015/0107397 A1    Apr. 23, 2015

(51) Int. Cl.
*B25J 19/00*      (2006.01)
*F16C 11/10*     (2006.01)
(Continued)

(52) U.S. Cl.
CPC ......... *B25J 19/0004* (2013.01); *B25J 17/025* (2013.01); *B25J 17/0241* (2013.01);
(Continued)

(58) Field of Classification Search
CPC .................................................. B25J 19/0004
See application file for complete search history.

(56) References Cited

U.S. PATENT DOCUMENTS 4,506,590 A * 3/1985 Miki .................... B25J 17/0241
                                                        192/30 W
2013/0340560 A1* 12/2013 Burridge .................. B25J 17/00
                                                        74/490.05

FOREIGN PATENT DOCUMENTS

DE           9315132 U1      12/1993
DE          19508328 A1       9/1996
(Continued)

OTHER PUBLICATIONS

International Preliminary Report on Patentability dated Dec. 16, 2014 from International Patent Application No. PCT/EP2012/002590 filed Jun. 15, 2012.
(Continued)

*Primary Examiner* — William Kelleher
*Assistant Examiner* — Gregory T Prather
(74) *Attorney, Agent, or Firm* — Sunstone IP

(57) ABSTRACT

A bidirectional pivoting joint comprises pivoting elements which are rotatable relative to one another, specifically in a coaxial arrangement, a cylindrical outer body and a cylindrical inner body and a locking device optionally locking and releasing the rotational movement. The locking device has an annular space between the outer body and the inner body. Provided between annular space surfaces, specifically an inner surface of the outer body and an outer surface of the inner body are radially narrowing and, on the other hand, radially wider, peripheral regions in alternating arrangement. Arranged in the annular space are at least two clamping members which are each adjustable in cross-section in the peripheral direction (u) of the annular space. In a holding state, each clamping member has a first said cross-section and lies in the narrowing peripheral regions against the outer body and the inner body. By this means, a self-holding clamping connection is established which blocks the relative rotational movement between the outer body and the inner (Continued)

Figure 1:
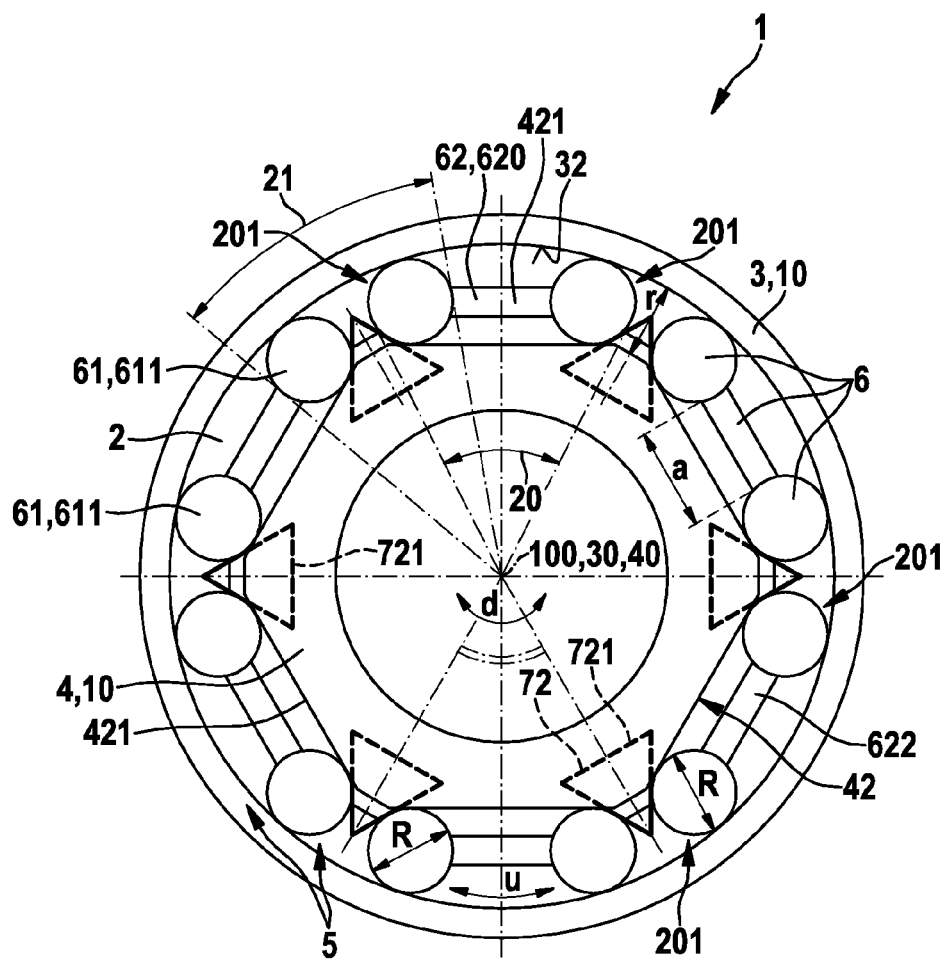

body in each rotation direction (d). In a releasing state, each clamping member has a second said cross-section by means of which the clamping connection is released in order to free the rotational movement. An actuating device of the pivoting joint is equipped with an actuating means which acts on the clamping members to establish, firstly, the holding state and, secondly, the releasing state. A holding and positioning device comprises a plurality of said pivoting joints.

25 Claims, 7 Drawing Sheets

(51) Int. Cl.
    *B25J 17/02*     (2006.01)
    *F16M 11/06*     (2006.01)
    *F16M 11/20*     (2006.01)
    *A61B 34/30*     (2016.01)

(52) U.S. Cl.
    CPC ............. *F16C 11/10* (2013.01); *F16M 11/06* (2013.01); *F16M 11/2007* (2013.01); *A61B 34/30* (2016.02); *Y10T 74/20329* (2015.01)

(56) References Cited

FOREIGN PATENT DOCUMENTS

DE          10209209 A1     2/2004
DE     102008023751 A1     11/2009

OTHER PUBLICATIONS

International Search Report dated Mar. 7, 2013 from International Patent Application No. PCT/EP2012/002590 filed Jun. 15, 2012.

* cited by examiner

BIDIRECTIONAL PIVOTING JOINT, AND A HOLDING AND POSITIONING DEVICE WHICH COMPRISES A PLURALITY OF SAID PIVOTING JOINTS

CROSS-REFERENCE TO RELATED APPLICATIONS

This application is a National Stage Application of PCT/EP2012/002590, filed Jun. 15, 2012, the subject matter of which is incorporated herein by reference in its entirety.

The invention relates to a bidirectional pivoting joint comprising a hollow cylindrical outer body having a hollow space, and a cylindrical inner body arranged in the hollow space, wherein the outer body and the inner body can be rotated with coaxial cylinder axes relative to one another about a joint axis, and a locking device which optionally locks and releases the rotational movement between the outer body and the inner body. The invention also relates to a holding and positioning device comprising a plurality of pivoting joints connected to one another and a control device for releasing and blocking the pivoting movements of the pivoting joints.

The bidirectional pivoting joint of the aforementioned type is a lockable rotary joint having joint elements which are rotatable relative to one another in both rotation directions equally about the joint axis and which are formed from an outer body and an inner body. The locking device of the pivoting joint is configured in order to lock and release relative rotary positions of the outer body and the inner body reached by means of rotation. In particular, the rotation concerns a restricted rotation understood to be a pivoting movement. The locked state is intended to withstand reliably the greatest possible torque load and the released state is intended to ensure optimum free rotation and the change between the locked and the released state should be achievable particularly easily and precisely. Such requirements are placed, in particular, on holding and positioning devices in which the pivoting joints are connected behind one another in series, in particular with six joints. Devices of this type form robot arms or jointed arms which are, in particular, components of medical device, for example, in the surgical field and which are intended to meet particular requirements of use and safety.

Known pivoting joints of this type are not satisfactory with regard to the stated requirements. Pivoting joints with frictionally engaged stepless locking (blocking) are known. Locking of this type is subject to particularly great wear and is also able to withstand only limited loads. In the presence of large, but also of small loads, frictionally engaged locking is susceptible to slippage caused by wear or dirt. This is helped by pivoting joints which are equipped with stepped or stepless snap locking systems (DE 102 09 209 A1). Known stepless locking systems based on friction, but also those with snap locking usually have to actuate a relatively large force as a result of hysteresis, particularly if joints are subjected to high loads before an unlocking process. In addition, the known pivoting joints are unsatisfactory with regard to controlling the locking and unlocking. In particular, simultaneous triggering of locking or unlocking, by hand or by automated actuation, of a plurality of joints that are linked to one another is impaired. The known joints are not sterilisable and not even disinfectable.

Objects of the invention are realising an aforementioned rotation-pivoting joint with stepless bidirectional rotation locking, the use and operation of which with regard simultaneously to loadability of the locking connection, lifespan, functional reliability, sterilisability, precise and largely hysteresis-free controllability of the operating states and robustness are to be improved. It should also be possible to execute the pivoting joint with a relatively small construction.

The aims of the invention are achieved in conjunction with the features of the aforementioned pivoting joint in that the locking device is provided by means of an annular space which is concentric with the joint axis and lies between the outer body and the inner body with radially narrowing and, by contrast, radially wider peripheral regions in an alternating arrangement between the annular space surfaces of the annular space, specifically between an inner surface of the outer body and an outer surface of the inner body, at least two clamping members distributed over the annular periphery of the annular space and arranged therein, said clamping members each having a cross-section being variable in the peripheral direction of the annular space, and an actuating device for setting the aforementioned variable cross-sections of the clamping members, wherein each clamping member assumes two states, namely a holding state determined by a first said cross-section of each clamping member in which each clamping member lies against the inner surface of the outer body and against the outer surface of the inner body in said narrowing peripheral regions which adjoin one another, so that a self-holding clamping connection is established capturing the clamping members between the inner surface and the outer surface, blocking the relative rotational movement between the outer body and the inner body in each rotation direction, and namely a releasing state determined by a second said cross-section of each clamping member in which the clamping connection is released in order to free up the relative rotational movement and wherein the actuating device comprises actuating means which acts on the clamping members to establish, firstly, the holding state and, secondly, the releasing state.

A holding and positioning device of the aforementioned type is distinguished in that the pivoting joints are each formed by a pivoting joint according to the invention.

The holding states of the clamping members bring about the locking of the pivoting joint. In the releasing states of the clamping members, the pivoting joint is unlocked. The invention achieves a series of advantages. In the locking positions, that is in the holding states of the clamping members, said clamping members are situated with non-deformable shape-maintaining parts in play-free seating between the joint elements, namely the outer body and the inner body. Form-fitting connections are created which block relative rotational movement in every rotation direction between the outer body and the inner body by clamping in the radially narrowing peripheral regions, even under particularly large applied moment. The form-fitting capture and clamping of the clamping member on both sides in the radially narrowing, wedge-like acting peripheral geometry between the outer body and the inner body is largely free from wear in the parts contacting one another. What is achieved is that, after relatively long use of the pivoting joint, it is ensured that a play-free locked state and, as a consequence, constant force conditions are maintained. A further substantial advantage lies in that the change-over between the holding state and the releasing state requires only a minimum state change, i.e. a very small cross-sectional change through, for example, simple length change in the clamping member in the peripheral direction of the concentric annular space. This means that each clamping member needs to be changed only minimally in the peripheral length dimension thereof, practically according to a secant line enclosed by the outer body, in order to free or block the rotational movement between the outer body and the inner body bidirectionally. Said cross-section change is brought about particularly easily and particularly reliably with the actuating means. The actuating means must only be configured such that, in the dimension corresponding to said secant, the clamping member is changed only to the slight extent that the clamping member comes free from the form-fitting connection on both sides in the peripheral direction of the annular space, i.e. from the captured position, with only the slightest play. Although the locking is configured to be self-holding, only a relatively small force is required for unlocking. The self-holding locking resists a torsional load to the highest degree. The pivoting joint according to the invention therefore meets particular safety requirements. This results in particularly simple and reliable control in order to bring about the holding state, the releasing state and the change between these two states by means of the actuating means, which can be realised correspondingly easily. Hysteresis is largely excluded. Furthermore, stepless locking is achieved, which ensures in every position of the concentrically mounted joint elements, matching force and geometry conditions so that the function of the pivoting joint remains reliable independently of the rotary position between the outer body and the inner body currently assumed for locking. Due to the minimal change in the geometry of the clamping member in the peripheral direction of the annular space which is sufficient for the changeover between the holding state and the releasing state, the control travel for the change between the two states is correspondingly small. The control system is substantially simplified, particularly with regard to the high control speed, that is, the particularly short response time. By use of a common control device, a plurality of pivoting joints connected in series one after another can be reliably and precisely operated simultaneously. The pivoting joint according to the invention can be sterilised, in particular, in an autoclave. This extends the usage possibilities. In particular, the joint can be used for bone surgery which places the highest sterility requirements.

Although the clamping member can be formed by any means, the cross-section thereof in the peripheral direction of the annular space, that is, transversely to the radial planes extending in the axial direction of the pivoting joint is changeable, a particularly preferred practical embodiment lies in that the clamping member is formed by two clampable clamping elements arranged offset in the peripheral direction of the annular space and a spacing means having a length with is changeable in the peripheral direction of the annular space, said spacing means spacing the two clamping elements apart from one another in the peripheral direction of the annular space and displacing said clamping elements relative to one another to establish at least one of the two positions, namely the holding position or the releasing position. The clamping elements are non-deformable parts of fixed form.

Particularly advantageously, the spacing means connecting the two clamping elements of the clamping member can be an actuator acting under force. The distance separating the clamping elements is then subject to a force-deflection function. Advantageously, the actuator is a spring means acting in the peripheral direction of the annular space. At least one compression spring is provided if the actuator is to be shortened against a spring force to establish the releasing state. The clamping elements of the clamping member can be connected to at least one tension spring if the spacing of the clamping elements is to be increased against a tensional force in order to bring about the releasing state. In general, any means which is suitable for pressing together or pressing apart the clamping member, that is, for applying the relevant force to the clamping elements is suitable as an actuator, namely in particular in place of a mechanical spring means, for example, a pneumatically or electrically operating means. It is useful in general, that the spacing means or the actuator is merely configured so as to hold the clamping elements in the clamping spaces, namely the narrowing peripheral regions.

A preferred embodiment consists in that the clamping elements of the clamping member are cylinder elements extending parallel to the joint axis. By selecting the length of the cylinder elements, for example, in the form of cylindrical rods, the size of the holding force in the holding state can be specifically established. The length of the contact surfaces/lines of the cylinder elements with the outer body inner surface or with the inner body outer surface is an essential measure of the holding force which can be contrived, in particular, to be at least substantially proportional to the length of the contact surfaces. Embodiments of clamping members with clamping elements which have a different geometry and strength suitable for form-fitting and clamping, in particular, for example balls, also come into consideration.

A preferred embodiment consists in that the annular space is subdivided into peripheral sections, each accommodating one said clamping member, wherein each peripheral section has two of the narrowing peripheral regions, each of which forms a clamping space which narrows the annular space in the radial dimension thereof. This embodiment is provided particularly in conjunction with the measure that each clamping member comprises a pair of clamping elements which, in order to establish the holding state, each reach into the two narrowing peripheral regions of a said peripheral section. Suitably, the outer surface of the inner body is formed by space partial surfaces which determine said peripheral sections of the annular space and, together with the inner surface of the outer body, form the narrowing peripheral regions. Suitably, the space partial surfaces of the inner body in the cross-section of rotation of the joint are determined at least partially by a polygonal line. In the same way, however, the inner surface of the outer body can be provided, in particular, as a polygonal surface. The polygonal surface always forms, in cooperation with the other annular space surface, the narrowing peripheral regions on, on the other hand, the wider peripheral regions. Said polygonal surfaces, preferably with straight or planar surfaces, are a general feature of the invention.

One embodiment consists in that the two clamping elements of said clamping member are each arranged on a space partial surface of two adjacent said space partial surfaces of said annular space surface, preferably at the outer surface of the inner body. Another embodiment provides that the two clamping elements of said clamping member are arranged on said common space partial surface of said annular space surface, preferably on the outer surface of the inner body.

Any actuating device, which shortens and/or elongates all the clamping members, can be provided in conjunction with the clamping members, so that said clamping members each change from the holding state to the releasing state and also, according to a possible embodiment, back into the holding state. For this purpose, means can be provided which act, for example, pneumatically, electromechanically or mechanically on the clamping members. A particularly preferred measure lies in that the actuating device has control elements which engage with said clamping elements in order to establish the holding state or the releasing state, wherein said clamping elements operate against the force of said spacing means actuator.

In particular, at least one control element is arranged at least partially within the annular space between two adjacent clamping elements. Preferably, in this embodiment, as also in the other embodiments, all the clamping members and/or control elements are similarly arranged and configured. The arrangement of the control element partially within the annular space is suitable such that, for unlocking from an almost-touching position with the clamping members or clamping elements, the control element comes into engagement with these. Advantageously, the control element is configured with a control profile which is chamfered and/or rounded such that a radial control movement of the control element into the annular space brings about a compression force directed transversely to this movement, preferably simultaneously, onto two adjacent clamping members and/or clamping elements in the annular space. For example, the control profile is formed by a ball-shaped, triangular, trapezoid or cylindrical control head. In any event, the control elements operating with a radial control movement also support an independent adjustment of the elements arranged in the annular space.

One embodiment consists in that said control element for two adjacent clamping elements is associated with at least one peripheral section of the annular space, said peripheral section being free from spacing elements of the clamping members. This embodiment is particularly advantageous in conjunction with adjacent clamping members, the two clamping elements of which are each arranged at one said partial surface of the outer surface of the inner body.

Another embodiment consists in that said control element for two adjacent clamping elements is associated with at least one annular space peripheral section of the annular space in which the spacing means of a said clamping member is arranged. This embodiment is suitable in particular for said clamping members, both clamping elements of which connected to the spacing means are arranged at two adjacent partial surfaces of the outer surface of the inner body.

Another embodiment consists in that at least one spacing means of a said clamping member is formed by a said control element. Thus, a control element can be, for example, an actuator which brings about the elongation and shortening of the clamping member for assuming the holding state or the releasing state.

An advantageous measure lies in that provided in the annular space is at least one chain-like row which is formed by said clamping elements, said spacing elements and said control elements, wherein the chain members, respectively adjacently, are linked to one another in the releasing state of the clamping members. For example, a single chain-like row is closed over the annular periphery. This closed row, similarly to partial rows, contributes particularly to the self-adjustment of the elements of the pivoting joint. During unlocking, however, interference between adjacent clamping members is prevented.

A particularly simple and preferred embodiment of the actuating device consists in that said actuating device has at least one control element which, for establishing the holding state or the releasing state, engages with associated said clamping members, is mounted on the inner body of the pivoting joint and is arranged to be actuatable transversely to the peripheral direction of the annular space.

A plurality, preferably all, of the control elements can be installed to be actuatable by means of a single control part which is arranged, in particular, in a hollow space of the inner body of the pivoting joint and is displaceable axially parallel to the cylindrical axis of the inner body. A control part of this type can be configured, for example, in the manner of a plunger with control surfaces which lie against parts, for example, control rods of associated control elements and converts axial movement of the control part (control body) into radial movement of the control elements. Particularly advantageously, control/contact surfaces are arranged at the periphery of the control part, said surfaces lying diagonally opposed, so as to bring about self-centring of the control part. In the arrangement between parts lying against the control surfaces, the control part is radially mounted almost without play.

Advantageously, an annular space surface bordering the annular space, specifically the inner surface of the outer body or the outer surface of the inner body, is a circle cylindrical shell surface, specifically in cooperation with the other annular space surface which is configured with the said polygonal surfaces or other surfaces widening/narrowing the annular space. A preferred embodiment consists in that the pivoting joint is configured with a plurality of said clamping members symmetrical relative to the joint axis. The symmetrical arrangement is particularly suitable for centring and adjusting the joint elements. Advantageously, the pivoting joint comprises at least six of the clamping members, which are arranged evenly distributed over the annular circumference of the annular space. Six clamping members, particularly in conjunction with six associated said polygonal surfaces, have proved to be particularly advantageous for optimising the size of the holding force. However, a pivoting joint according to the invention with, for example, three similar clamping members or associated narrowing surfaces also offers said advantages.

In a basic embodiment of the pivoting joint according to the invention, the outer body can be radially mounted, exclusively by means of the clamping members, on the inner body. The annular space and the clamping members are then adapted and designed such that, in the releasing state, a minimal, just sufficient bearing play is provided between the clamping members and the outer body in order to permit free rotation and to mount the outer body and the inner body in a concentric arrangement on one another. In particular, cylindrical elements in the form of cylindrical rods, specifically the clamping elements of the clamping members, then form the bearing pins of a pin bearing between the two bodies. In principle, a minimum play is generally set between the inner surface of the outer body and the clamping members, in particular the clamping elements of the clamping members lying, in the releasing state, against the outer surface of the inner body, such that it just permits free rotation.

Suitably, the outer body and the inner body can be mounted pivotably/rotatably on one another by means of at least one radial bearing arranged outside the annular space. The clamping members then remain free from the aforementioned bearing function.

A particular embodiment of the inventive holding and positioning device consists in that the control device comprises control parts corresponding to the number of pivoting joints connected in series to one another and which are each formed by a control body having at least one control contour, wherein each control body which is axially actuatable in the direction of the associated joint axis and belongs to a pivot joint, has at least one control surface oriented with a flat course to the joint axis, which, according to the axial actuation position of the control body, controls at least one associated control element of the associated pivoting joint which is movable transversely to the joint axis for releasing or blocking the pivoting movement.

A holding means which applies holding forces directed toward the inner body to all the clamping members can be arranged between the outer body and the inner body of the pivoting joint. A holding means of this type is advantageously formed by an elastic holding means, suitably by a worm spring which is applied to all the clamping members, closed over the full circumference of the annular space. For example, the holding means is applied to the said clamping elements of the clamping members so that all the clamping elements remain undisturbed by said cross-sectional change of the clamping members in secure contact with the outer surface of the inner body.

Figure 2:
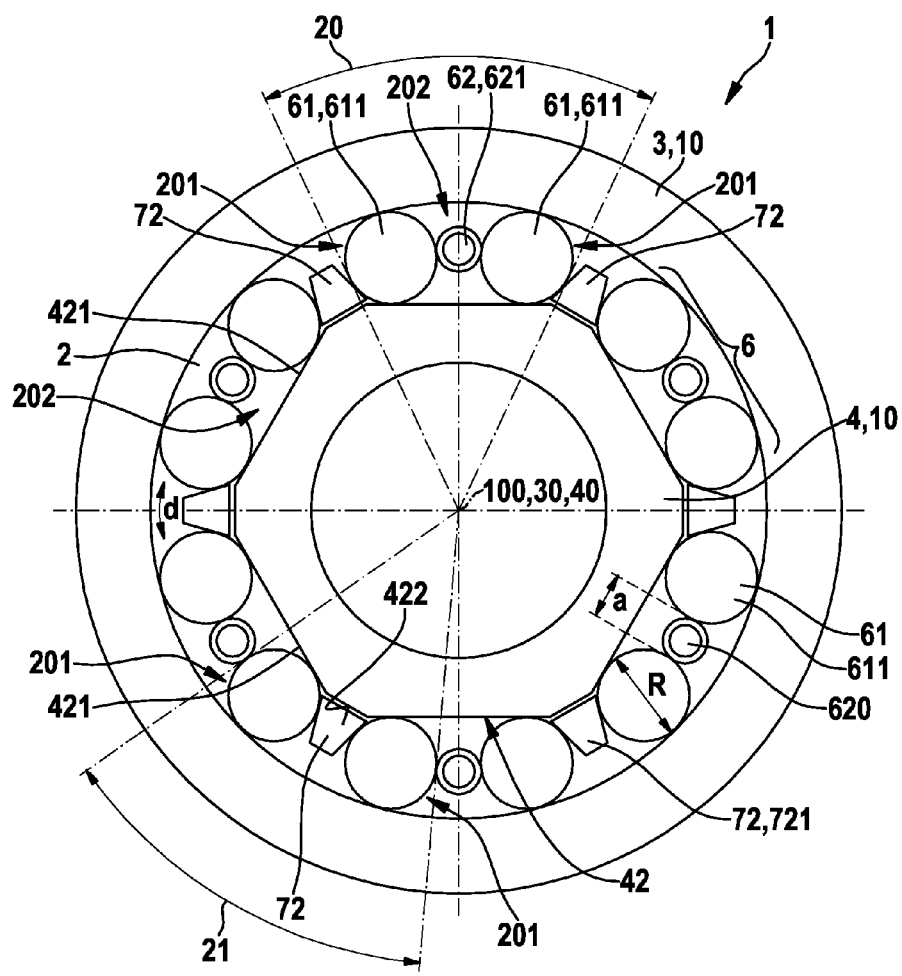
Figure 3A:
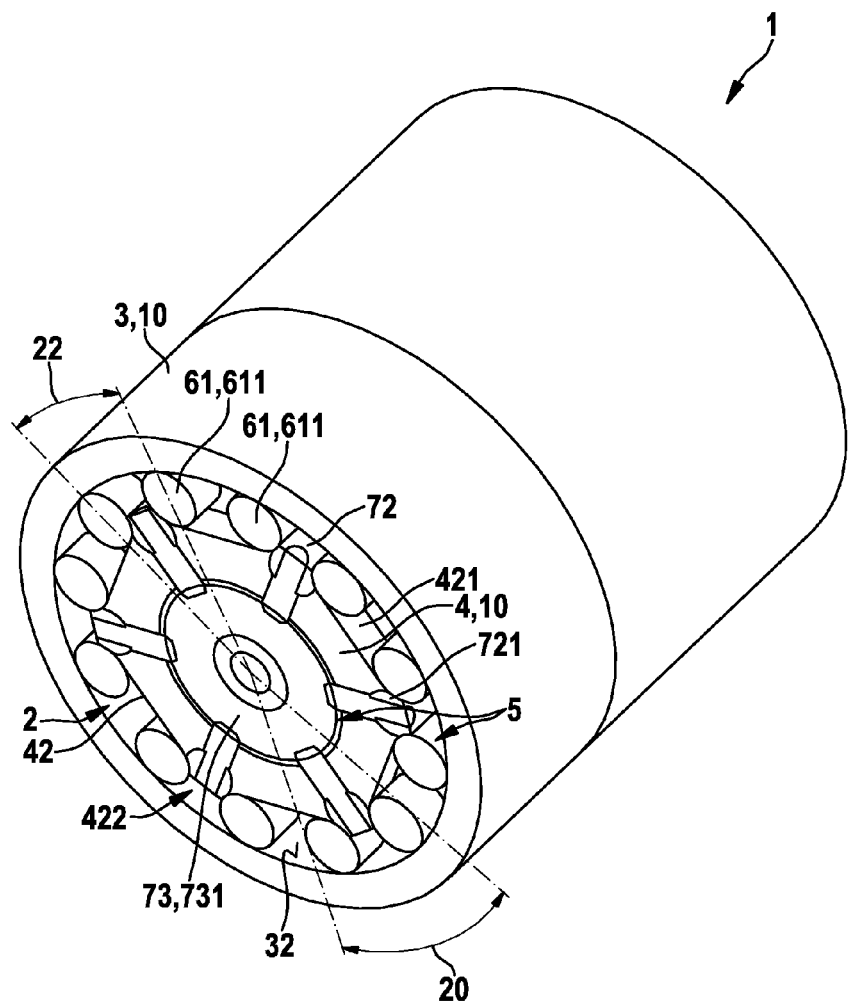
Figure 3B:
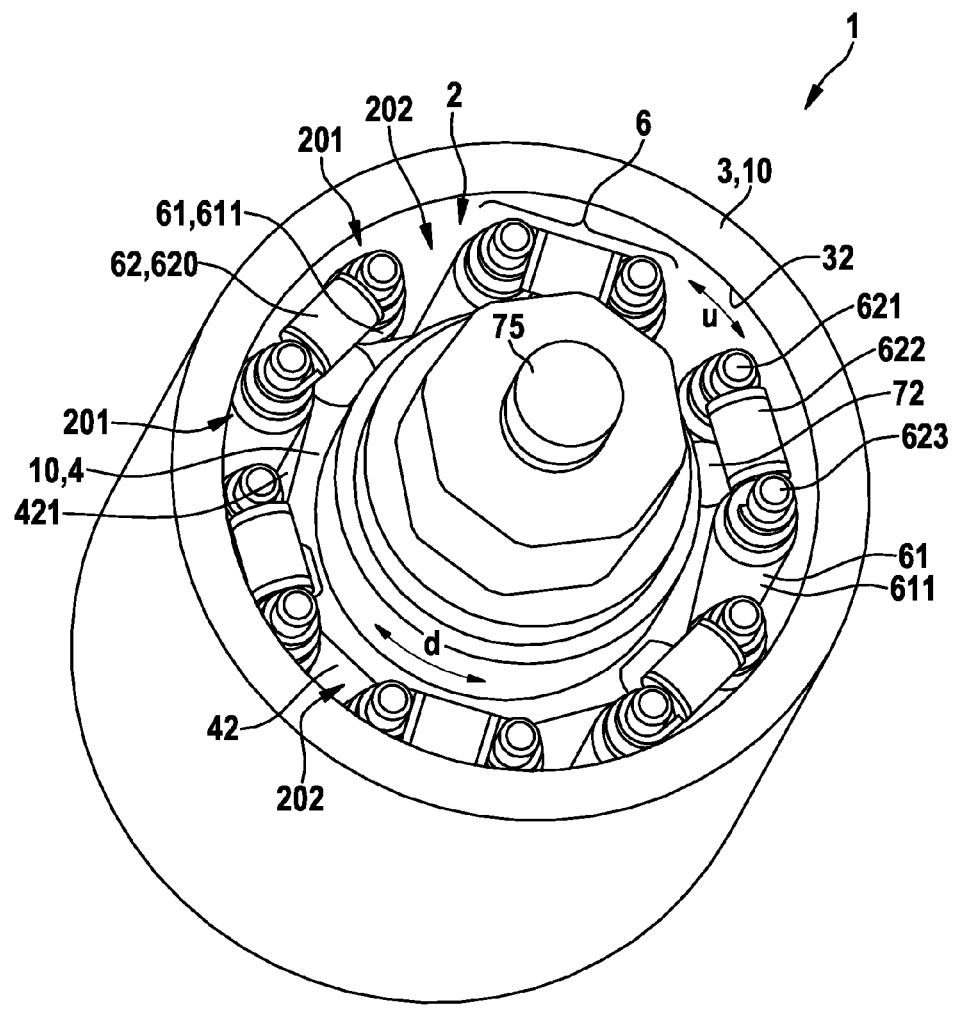
Figure 3C:
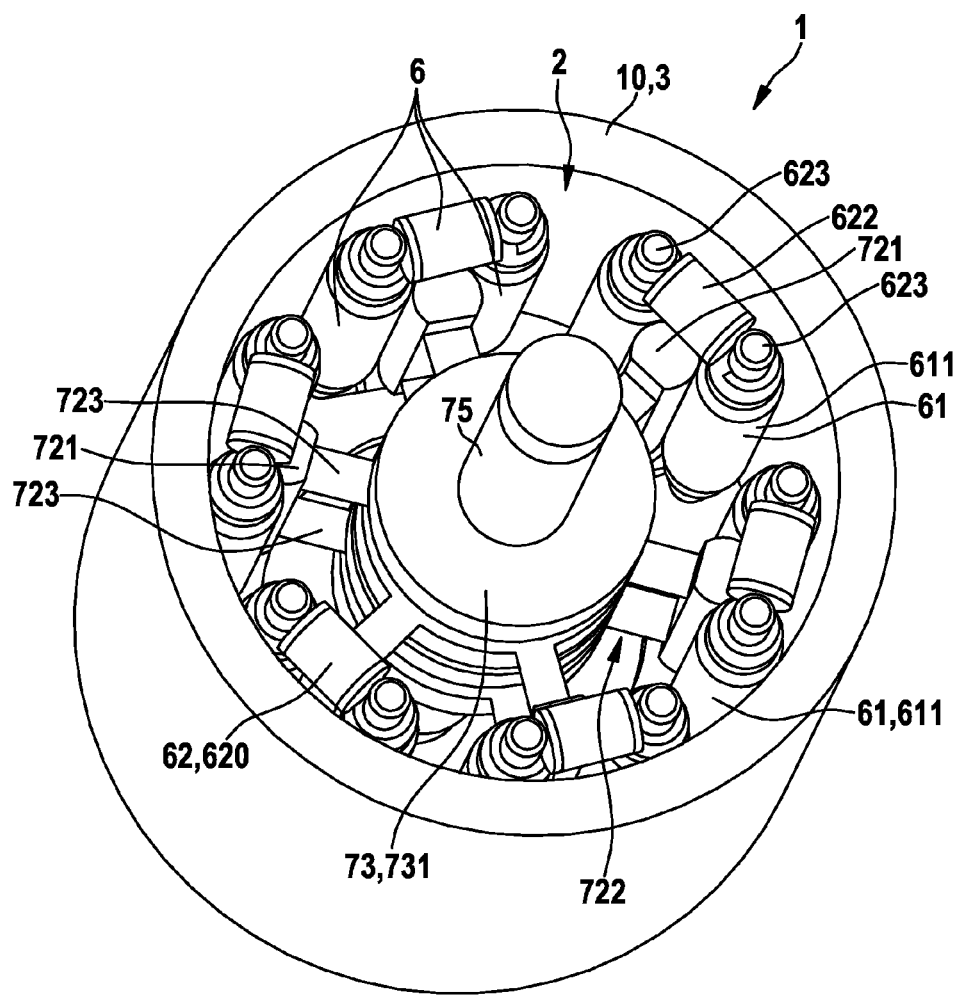
Figure 3D:
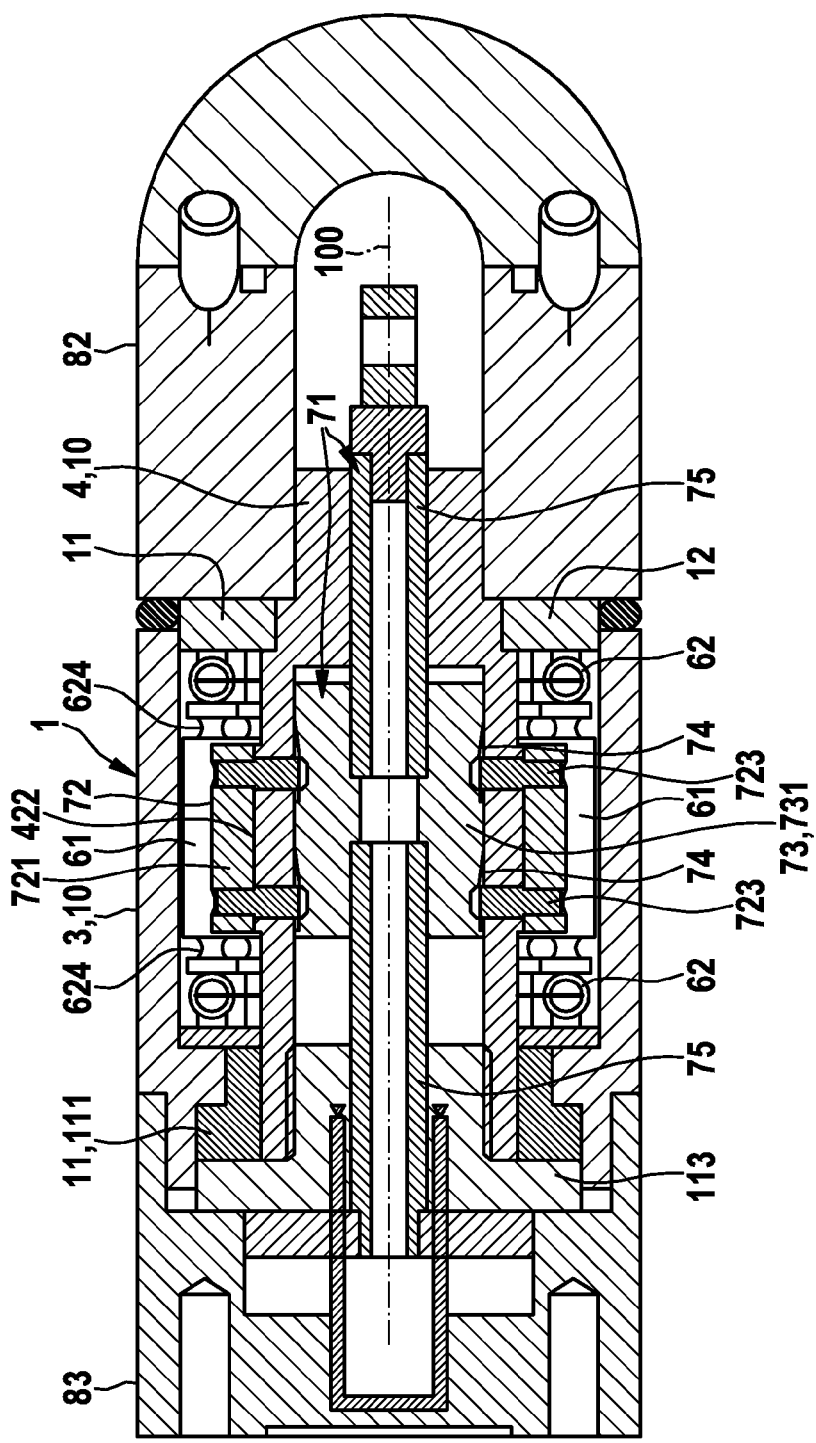

The subclaims are directed to the aforementioned and other suitable and advantageous embodiments of the invention. Only particularly suitable and advantageous embodiments and possibilities are described in greater detail in the following description of the exemplary embodiments shown in the schematic drawings. Each individual or detailed embodiment described within an exemplary embodiment is described as an independent detail example for other embodiments and forms which are not or not completely described and fall within the invention. In particular, a feature of this type is identified as a general feature which also contributes, in isolation from other features of a combination or an exemplary embodiment, to the inventive success of the general teaching of the invention and, in particular, according to a main claim. In the drawings:

FIGS. 1 and 2 show, in a front view, pivoting joints according to the invention in a first design, FIGS. 3A to 3C show axonometric views of a pivoting joint according to the invention in a second design with a sectional view according to FIG. 3A and front views according to FIGS. 3B and 3C, FIG. 3D shows a longitudinal section of a pivoting device of FIGS. 3A to 3C, and FIG. 4 shows a holding and positioning device according to the invention having pivoting joints according to the invention.

In all the figures, regardless of changes of design, for the same parts which have the same effect and are of equal value according to the invention, the same reference signs are used.

FIGS. 1 and 2 show pivoting joints 1 according to the invention, each of which comprise, in concentric arrangement, an outer body 3 and an inner body 4, an annular space 2 formed between the two bodies 3, 4 and clamping members 6 arranged therein. The outer body 3 and the inner body 4 are each formed by a hollow body having a circle cylindrical form wherein the cylinder axes 30, 40 coincide coaxially in a joint axis 100 of the pivoting joint 1. The outer body 3 and the inner body 4 are joint elements 10 which are rotatable about the joint axis 100 relative to one another in both directions d.

Six identical clamping members 6 are provided, evenly distributed round the periphery of the annular space 2 offset in the peripheral direction u thereof, and are able to form a radial bearing for mounting the two bodies 3, 4 on one another. However, the pivoting joints 1 of FIGS. 1, 2 should preferably be provided with radial bearings which are arranged outside the annular space 2 in front regions not shown in FIGS. 1, 2. As a general feature, radial bearings are provided, as can be configured, for example, according to FIG. 3D.

The annular space 2 extends in the direction of the pivot axis 100 with a particular annular space length corresponding to the cylinder lengths of the two bodies 3, 4. In the radial dimension, the annular space 2 is configured particularly with adaptation to the clamping members 6.

The outer body 3 has a cylinder inner surface (circle cylindrical inner surface) 32 which is circular in cross-section of the cylinder. By contrast, the cylinder outer surface 42 of the inner body 4 is formed by six identical planar space partial surfaces 421, wherein in the cylinder cross-section, a polygonal line with six identical straight polygonal sections corresponding to the space partial surfaces 421 is to be seen. Arranged between the polygonal sections are identical surface intermediate sections 422 which are short relative to the said polygonal section length. It can be seen that, relative to the inner surface 32 of the outer body 3, the space partial surfaces 421 form secant surfaces which form, in alternating manner over the annular periphery of the annular space 2, radially narrowing and widening peripheral regions 201, 202. Thus the narrow or narrowing peripheral regions 201 and between these, the widened or widening peripheral regions 202 belong to each space partial surface 421 as a pair.

Each clamping member 6 is arranged on a said space partial surface 421 associated therewith. It comprises two non-deformable clamping elements 61 associated with the narrow peripheral regions 201 and a spacing means 62 connected thereto which spaces the two clamping elements 61 at a distance a in the peripheral region 202. The distance a is subject to a force-deflection function determined by the spacing means 62. The spacing means 62 is an actuator 620, specifically in the example of FIG. 1, a compression spring 621. A compression spring 621 of this type can also be understood to mean a plurality of compression springs arranged in parallel. For example, one compression spring each is arranged at the axial longitudinal ends of a clamping element pair. The clamping elements 61 are rod-like cylindrical elements 611 with a circular cross-section which extend parallel to the joint axis 100. The clamping elements 61 have a circle diameter R which is greater than the smallest radial dimension of the narrowing peripheral regions 201, but is smaller than the radial width of the associated peripheral region 202, which widens between the narrowing peripheral regions 201. Clamping elements with such a larger diameter of an element with a circular cross-section or, in general, with a larger diameter than the narrowing diameter are a general feature.

The clamping member 6 is configured such that it assumes two states under the effect of the spacing means 62, i.e. a holding state and a releasing state. The holding state is determined in that the two clamping elements 61 of the clamping member 6 appropriately reach into the narrowing peripheral regions 201. The clamping element 61 thus lies in positive-locking manner against the outer body inner surface 32 and against the associated space partial surface 421 of the inner body 42, specifically in tangential contact. The holding state is thereby brought about and is maintained in that the spacing means 62 forces the clamping elements 61 apart at a greater distance a, so that the clamping elements 61 are caught in the narrow peripheral regions 201. The result is that the outer body 3 and the inner body 4 in the holding state described, which is assumed by all the clamping members 6 simultaneously, are locked to one another in twistproof manner and are therefore blocked against any relative rotational movement. The releasing state arises in the exemplary embodiment of FIGS. 1 and 2 through a reduction in the distance a of the spacing means 62. How this is achieved will now be described.

It is clear that the clamping member 6 is adjustable in cross-section depending on the distance a which corresponds to the direction u of the periphery of the annular space 2. In the holding state, this cross-section is at a maximum; and the releasing state is brought about already by a minimal reduction in the cross-section, that is, a minimal reduction in the distance a, wherein both clamping elements 61 are forced out of both the peripheral regions 201 simultaneously and preferably to the same extent. Thus a general feature consists therein that the peripheral region 201 opens into the peripheral region 202, becoming larger according to its narrowing. As a consequence, the clamping elements 61 become progressively free during unlocking. In the exemplary embodiment, the geometry of the narrowing peripheral regions 201 and, respectively, of the correspondingly widening transition into the peripheral region 202 through the secant-like position of the space partial surfaces 421 to the circular form of the other annular space surface is achieved. The circular cross-section of the cylindrical elements 611 cooperates with this geometry, which forms a general feature, said geometry lying in the holding state only tangentially against one space partial surface and the circular contour of the other annular space surface.

The space partial surfaces 421 define peripheral sections 20 of the annular space 2. Adjacent peripheral sections 20 are each separated from one another by a peripheral section 21 which encloses the intermediate surface section 422 and is free from spacing means 62 of the clamping members 6. Thus, the peripheral sections 21 are located between the clamping members 6.

A radially guided control element 72 engages in each peripheral section 21 with a control head 721 which, in the rotational cross-section of the joint of FIG. 1, is triangular-shaped, and in FIG. 2 is trapezium-shaped. The control elements 72, configured in each case identically, are mounted by means of radial guides (not shown) on the inner body 4 and for locking or unlocking of the pivoting joint 1 are movable backward and forward in the direction r. FIGS. 1 and 2 each show the locking state of the pivoting joint 1 with the holding states of all the clamping members 6. The control elements 72 are in corresponding conforming positions in which they permit the unimpeded form-fit/clamping seating of the clamping elements 61 in the peripheral regions 201, wherein said control elements are in an almost touching or quasi touching state with the clamping elements 61, as shown in FIGS. 1 and 2. This quasi touching is a preferred general feature of the invention. Therefore, defined inner positions, namely starting positions of the control elements 72 are configured for unlocking. Advantageously, the control head 721 of the control element 72 extends almost over the axial length of the associated clamping elements 61. This is a general feature.

According to the exemplary embodiments of FIGS. 1 and 2, each control element 72 is arranged at least partially within the annular space 2 between two adjacent clamping elements 61 or clamping members 61 during the holding states of the clamping members 6. Not shown in detail in FIGS. 1 and 2 is that the control elements 72 can be moved radially outwardly out of said starting position uniformly and evenly further into the annular space 2, i.e. into outer positions, namely with an actuating device (not shown in FIGS. 1 and 2) which holds the control elements 72 uniformly in the inner or outer positions. This is a general feature.

It can be seen that, by means of the control elements 72 placed in the outer position, the clamping elements 61 are each released, against the compression force of the actuator 620, out of the clamping position in order to bring about the releasing state. Due to the previously described geometrical properties, the radial control movement can remain minimal and is supported by the described shapes of the control head 721. The or each arrangement with which each control element acts simultaneously on two clamping members is a general feature. A decoupling of adjacent clamping members 6 is achieved in that movements/cross-section changes in the clamping members 6 are dominated by the control elements 72. Restoring forces of adjacent clamping members 6 are free from interference.

It is also apparent that, during the releasing states, by means of a closed ring arrangement, namely a closed row comprising the clamping elements 61, the spacing means 62 and the control elements 72, the clamping members 6 and the control elements 72 are in connection with one another through contact.

A pivoting joint 1 of FIGS. 3A to 3D according to the invention described below comprises, like the pivoting joints described above, in the same way, an outer body 3, an inner body 4 with six space partial surfaces 421, an annular space 2 correspondingly subdivided with peripheral regions 201 and 202, and clamping members 6 arranged therein. In the following, only differences and further details will be described.

The annular space 2 is subdivided into six peripheral sections 20 with each of which a clamping member 6 with two clamping elements 61 and a spacing means 62 are associated. The two clamping elements 61 of a clamping member 6 are each arranged on said space partial surface of two adjacent space partial surfaces 421. The spacing means 62 of each clamping member 6 is arranged in a peripheral section 22. Each clamping member 6 therefore extends in the peripheral direction u of the annular space 2 over a corner region, specifically an intermediate surface section 422 between adjacent space partial surfaces 421. The peripheral section 22 corresponds to this corner region.

The spacing means 62 is an actuator 620 applying a tensional force, for example, as in FIGS. 3B and 3C, a pair of tensional springs 622 which connect front-side longitudinal ends of the two clamping elements 61 of the clamping member 6 to one another. As FIGS. 3C and 3B show, cylinder elements 611 have axial bolts 623 to which the tension springs 622 are fastened with spring eyes.

Similarly configured control elements 72 are each associated with the peripheral section 22 of the annular space 2. The control elements 72 have a cylindrical control head 721 which is circular in the operational cross-section and a control foot 722 with two control pins 723. By means of the control pins 723, the control element 72 is guided radially movable on the inner body 4. The axial length of the control head 721 corresponds to the length of the associated clamping elements 61.

FIGS. 3A and 3B show the pivoting joint 1 in the locking state. It can be seen from FIG. 3D that the holding states of the clamping members 6 are brought about in that the control heads 721 of the control elements 72 are currently not in engagement or contact with the clamping elements 61, so that the clamping elements 61 of each clamping member 6 are pressed, by means of the spacing means 62, through tensional force into the narrowing peripheral regions 201. The result is the previously described positive locking/ clamping-fitting with tangential contact.

FIG. 3C represents the unlocked pivoting joint 1 with the release states of the pivoting members 6. In order to illustrate the representation, the pivoting joint 1 in FIG. 3C is freed from the inner body 4. As distinct from FIG. 3B, the control elements 72 are driven radially outwardly out of their identical inner positions into identical outer positions. Each control element 72 engages with a rounded surface of the control head 721 between the associated two clamping elements 61 so that said clamping elements are pushed against the tensional force of the tension springs 622 in the peripheral direction u of the annular space 2 and consequently come free from the peripheral regions 201.

FIGS. 3C and 3D show an actuating device 7 with an actuating means 71 which acts on the clamping members 6 to establish, firstly, all the holding states and, secondly, the release states.

The actuating means 71 comprises a control part 73 and control rods 75. The control part 73 is arranged axially displaceable in the hollow space of the inner body 4. The control part 73 is configured as a cylindrical control body 731, which is firmly attached to two control rods 75 which extend in the joint axis 100. The axial guidance of the control part 73 can be configured by means of radial mounting of the control rods 75 on both front ends of the pivoting joint 1.

As FIGS. 3C and 3D show, the control body 731 is provided on its cylindrical surface with control surfaces 74 which are associated with the control elements 72. The control surfaces 74 extend flat to the joint axis 100, specifically in the exemplary embodiment, with identical surfaces, that is, with straight, flat inclined surfaces. Each pair of inclined surfaces is associated with the two control rods pins of a control element 72. Furthermore, the control surfaces 74 are arranged at the periphery of the control part 73 in pairs, diagonally opposing one another.

Figure 4:
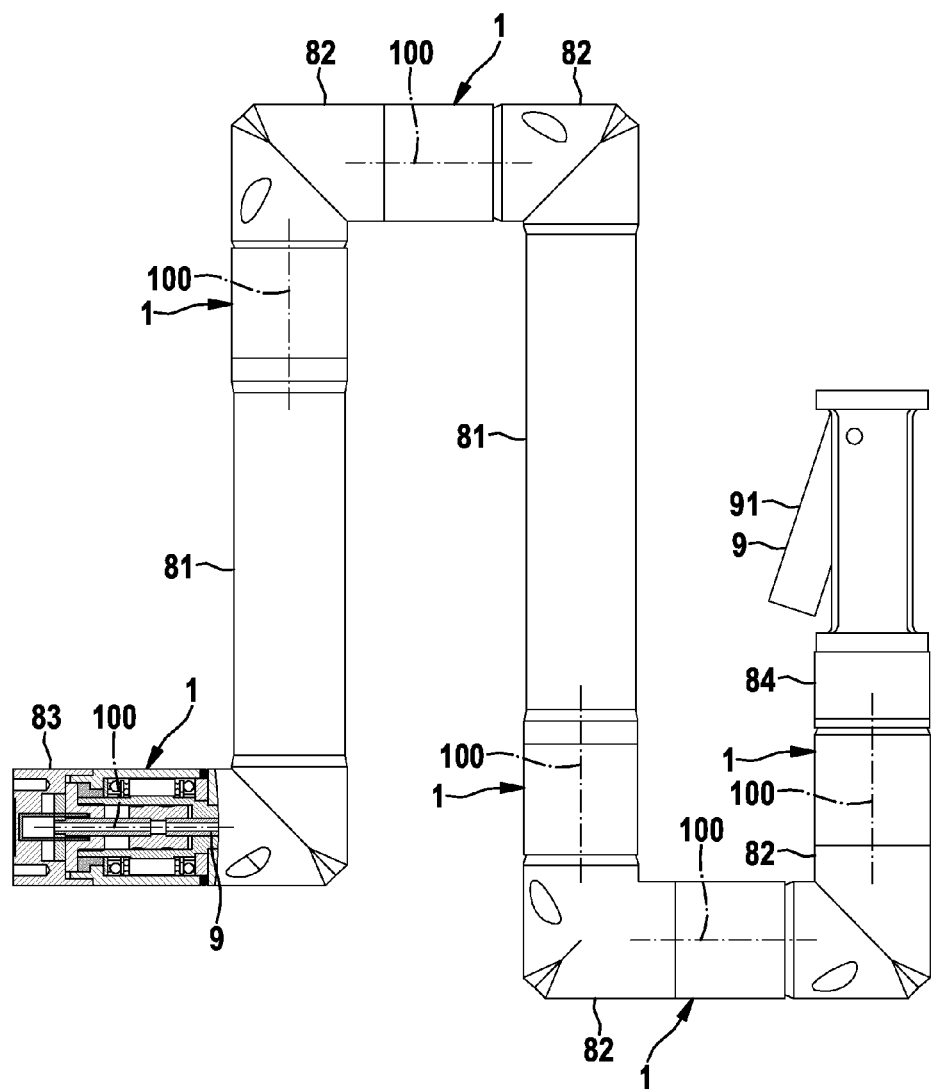

The pivoting joint 1 shown in FIG. 3D is a component therein of a holding and positioning device 8, as shown by way of example in FIG. 4. The holding and positioning device 8 has, at a fastening end thereof, a fastening piece 83 and, at an operative end, an attachment piece 84. FIG. 3D shows the fastening end. The pivoting joint 1 according to FIG. 3D is placed between the fastening piece 83 and an end piece 82. The connection to the fastening piece 83 and the end piece 82 is created by means of radial bearings 11. An end-side radial bearing 111, fastened by means of an end nut 113, simultaneously forms an axial bearing and, at the corner, a bearing ring forming an axial bearing 12 is provided.

As FIG. 3D shows, the axial bolts 623 of the clamping elements 61 are each formed with a waist 624 which is situated between the cylinder element 611 and the fastening site for the tension springs 622. The waists 624 accommodate a holding means, specifically an elastic tensioning means laid round all the clamping members 6, for example in the form of annular, closed worm springs, each of which are placed over the waists 624 at the end of the pivoting joint 1. The two worm springs are not shown in FIG. 3D, nor in the remaining drawings.

According to FIG. 4, the holding and positioning device 8 comprises six pivoting joints 1 according to the invention.

As is known per se, the pivoting joints 1 are connected to one another by means of tubular 90° corner pieces 82 and tubular arms 81. The device 8 is provided at the operative end, for example, with the gripping and attachment piece 84, which is configured for attaching to a device or the like (not shown) to be connected. FIG. 4 shows the device 8 in the non-pivoted state. This means that the joints and all the arms and pieces lie with their axes in one plane (the plane of the drawing page).

The device 8 is equipped with a control device 9. A control device of this type comprises, as known, a rod assembly with control rods 75 which extend in the pivoting joints 1 and the tubular arms 81 and are connected to one another in the end pieces 82 by means of rocker elements (not shown) in order to transmit or deflect axial movements of the rods 75 at an angle of 90°.

A peculiarity of the holding and positioning device 8 according to the invention lies in that the pivoting joints 1 according to the invention realise the advantages for handling and operating the device 8 achieved therewith and that the control device 9 is significantly improved. Thus, the control device 9 comprises the control parts 73 according to the number of pivoting joints 1 connected in series to one another. A control part 73 of this type in each pivoting joint 1 is distinguished, in general, in that it converts an axial movement coinciding with the joint axis 10 into radial control movements of the control elements 72. The control parts are, as described in relation to FIG. 3D, simple control bodies 731 which have control surfaces 74 oriented with a flat course to the joint axis 100, each of which is associated singly or multiply to a control element. In the exemplary embodiment of FIG. 3D, two identically-acting control surfaces 74 are associated with each control element 72, specifically with the control pins 723 of the control element 72.

As described in general and using the exemplary embodiments, the control path of the control elements 72 can be configured to a minimum dimension, i.e. according to a particularly flat course, of a in particular straight incline of the control surface 74. Suitably, each flat control surface 74 ends at the end side in a straight surface section parallel to the joint axis. This can be configured so small axially, in particular adapted to the geometry of the control feet 722, that the control elements 72 are securely seated in their end positions (inner positions/outer positions) and thus the axial response distance is reduced to a minimum.

As usual, the rod assembly operates on the fastening end of the device 8 against a restoring member (not shown in FIGS. 3D, 4), for example against a compression spring device fastened to a fastening surface (not shown). The fastening piece 83 is configured for attachment, for example, by a screw connection, to the fastening surface. The gripping/attachment piece 84 is provided with a movable actuating element 91 which is configured, as is per se known, for axial displacement of the control rods 75 of the control device 9.

As shown in FIG. 3D in conjunction with FIG. 4, the control rods 75 of the control device 9 connect in a mechanically simple manner to the control part 73, specifically for example in that the axial ends of the control part 73 are each firmly connected to the control rods 75. Suitably, this connection can be an adjustable connection, possibly provided only on one side. This general feature of the invention can be realised, for example, by means of at least one threaded connection.

The invention claimed is:

1. Bidirectional pivoting joint, comprising a hollow cylindrical outer body having a hollow space, and a cylindrical inner body arranged in the hollow space, wherein the outer body and the inner body can be rotated with coaxial cylinder axes relative to one another about a joint axis, and a locking device which optionally locks and releases the relative rotational movement between the outer body and the inner body, characterized in that the locking device is provided by means of an annular space which is concentric with the joint axis and lies between the outer body and the inner body with radially narrowing and, by contrast, radially wider peripheral regions in an alternating arrangement between the annular space surfaces of the annular space, specifically between an inner surface of the outer body and an outer surface of the inner body, at least two clamping members distributed over the annular periphery of the annular space and arranged therein, said clamping members each having a cross-section being variable in the peripheral direction (u) of the annular space, and an actuating device setting the aforementioned variable cross-sections of the clamping members, wherein each clamping member assumes two states, namely a holding state determined by a first said cross-section of each clamping member in which each clamping member lies against the inner surface of the outer body and against the outer surface of the inner body in said narrowing peripheral regions which adjoin one another, so that a self-holding clamping connection is established capturing the clamping members between the inner surface and the outer surface, blocking the relative rotational movement between the outer body and the inner body in each rotation direction (d), and namely a releasing state determined by a second said cross-section of each clamping member in which the clamping connection is released in order to free the relative rotational movement and wherein the actuating device comprises an actuating means which acts on the clamping members to establish, firstly, the holding state and, secondly, the releasing state, wherein at least one said clamping member is formed by two clampable clamping elements arranged offset in the peripheral direction (u) of the annular space and a spacing means having a length which is changeable in the peripheral direction (u) of the annular space, said spacing means spacing the two clamping elements apart from one another in the peripheral direction (u) of the annular space and displacing said clamping elements relative to one another to establish at least one of the two positions, that is the holding position or the releasing position, and wherein the actuating device has at least one control element which engages in associated said clamping members to establish the holding state or the releasing state, wherein the control element is mounted on the inner body and is arranged actuatable transversely to the peripheral direction (u) of the annular space.

2. Pivoting joint according to claim 1, characterized in that the annular space is subdivided into peripheral sections, each accommodating one said clamping member, wherein each peripheral section has two of the narrowing peripheral regions.

3. Pivoting joint according to claim 2, characterized in that each clamping member comprises a pair of clamping elements which, in order to establish the holding state, each reach into the two narrowing peripheral regions of a said peripheral section.

4. Pivoting joint according to claim 3, characterized in that an annular space surface of the annular space, that is the outer surface of the inner body or the inner surface of the outer body is formed by space partial surfaces which determine said peripheral sections of the annular space and, together with the other annular space surface of the annular space, form the narrowing peripheral regions.

5. Pivoting joint according to claim 4, characterized in that the two clamping elements of a clamping member are each arranged on a space partial surface of two adjacent said space partial surfaces (FIGS. 3A-3D).

6. Pivoting joint according to claim 4, characterized in that the two clamping elements of a clamping member are arranged on a common said space partial surface (FIGS. 1, 2).

7. Pivoting joint according to claim 4, characterized in that the space partial surfaces are formed by a polygonal line which at least partially borders the associated annular space surface.

8. Pivoting joint according to claim 1, characterized in that one of the annular space surfaces bordering the annular space is a circle cylindrical shell surface.

9. Pivoting joint according to claim 1, characterized in that the clamping elements of the clamping member are cylinder elements extending parallel to the joint axis.

10. Pivoting joint according to claim 1, characterized in that the spacing means connecting the two clamping elements of a said clamping member is an actuator operating under force, wherein the spacing (a) separating the clamping elements is subject to a force-deflection function.

11. Pivoting joint according to claim 10, characterized in that the actuator is a spring means acting in the peripheral direction (u) of the annular space.

12. Pivoting joint according to claim 10, characterized in that the actuator places the two associated clamping elements into at least one of the two states by means of the force acting in the peripheral direction (u) of the annular space, that is, into the holding state or into the releasing state and that the actuating device has control elements which engage with said clamping elements in order to establish the holding state or the releasing state and act against the forces of the actuators.

13. Pivoting joint according to claim 12, characterized in that at least one control element is arranged at least partially within the annular space between two adjacent clamping elements.

14. Pivoting joint according to claim 12, characterized in that said control element is associated with at least one peripheral section of the annular space, said peripheral section being free from spacing means of the clamping members.

15. Pivoting joint according to claim 12, characterized in that at least one peripheral section of the annular space in which the spacing means of a said clamping member is arranged, is associated with a said control element.

16. Pivoting joint according to claim 12, characterized in that at least one spacing means of a said clamping member is formed by a said control element.

17. Pivoting joint according to claim 12, characterized in that at least one chain-like series having chain members formed by said clamping elements, said spacing means and said control elements is arranged in the annular space, wherein in the releasing state of the clamping members, the chain members are linked to one another.

18. Pivoting joint according to claim 1, characterized in that arranged between the outer body and the inner body of the pivoting joint is a holding means which applies to all the clamping members a holding force directed toward the inner body.

19. Pivoting joint according to claim 18, characterized in that the holding means is formed by an elastic tensioning means laid round all the clamping members.

20. Pivoting joint according to claim 1, characterized in that a plurality of said control elements is actuatable by means of a control part which is arranged within a hollow space of the inner body and is displaceable along the cylinder axis of the inner body.

21. Pivoting joint according to claim 1, characterized in that the pivoting joint is configured with a plurality of said clamping members symmetrical to the joint axis.

22. Pivoting joint according to claim 1, characterized in that the pivoting joint comprises at least six of the clamping members which are arranged evenly distributed over the annular periphery of the annular space.

23. Pivoting joint according to claim 1, characterized in that the outer body and the inner body are rotatably mounted on one another by means of radial bearings arranged outside the annular space.

24. Holding and positioning device, comprising a series of mutually connected pivoting joints, each having a joint axis and a control device for simultaneous releasing and blocking of the pivoting movements of the pivoting joints in each case, characterized in that the pivoting joints are each formed by a pivoting joint according to claim 1.

25. Holding and positioning device according to claim 24, characterized in that the control device comprises control parts corresponding to the number of pivoting joints connected in series to one another, said control parts each being formed by a control body having at least one control contour, wherein each control body which is axially actuatable in the direction of the associated joint axis and belongs to a pivot joint, has at least one control surface which, according to the axial actuation position of the control body, controls at least one associated control element which is movable transversely to the joint axis for releasing or blocking the pivoting movement.

* * * * *